(12) United States Patent
Cognet et al.

(10) Patent No.: US 11,260,006 B2
(45) Date of Patent: Mar. 1, 2022

(54) COSMETIC COMPOSITION COMPRISING AN ANIONIC SURFACTANT, AT LEAST 3.5% BY WEIGHT OF A FATTY ACID AND AN ANTIDANDRUFF AGENT

(71) Applicant: L'OREAL, Paris (FR)

(72) Inventors: Marie Cognet, Saint-Ouen (FR); Estelle Mathonneau, Saint-Ouen (FR); Miao Wang, Clark, NJ (US); Christelle Morvan, Saint-Ouen (FR); Morgan Durand, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/062,268

(22) PCT Filed: Dec. 13, 2016

(86) PCT No.: PCT/EP2016/080799
§ 371 (c)(1),
(2) Date: Jun. 14, 2018

(87) PCT Pub. No.: WO2017/102728
PCT Pub. Date: Jun. 22, 2017

(65) Prior Publication Data
US 2018/0369089 A1    Dec. 27, 2018

(30) Foreign Application Priority Data
Dec. 15, 2015  (FR) ...................... 1562405

(51) Int. Cl.
| *A61K 8/36* | (2006.01) |
| *A61K 8/46* | (2006.01) |
| *A61Q 5/00* | (2006.01) |
| *A61K 8/44* | (2006.01) |
| *A61K 8/34* | (2006.01) |
| *A61K 8/41* | (2006.01) |
| *A61K 8/49* | (2006.01) |

(52) U.S. Cl.
CPC ............ *A61K 8/361* (2013.01); *A61K 8/342* (2013.01); *A61K 8/416* (2013.01); *A61K 8/44* (2013.01); *A61K 8/463* (2013.01); *A61K 8/466* (2013.01); *A61K 8/4913* (2013.01); *A61K 8/4926* (2013.01); *A61K 8/4933* (2013.01); *A61Q 5/006* (2013.01)

(58) Field of Classification Search
None
See application file for complete search history.

(56) References Cited

U.S. PATENT DOCUMENTS

| 3,472,840 A | 10/1969 | Stone et al. |
| 3,589,978 A | 6/1971 | Kamal et al. |
| 3,910,862 A | 10/1975 | Barabas et al. |
| 4,031,307 A | 6/1977 | DeMartino et al. |
| 4,131,576 A | 12/1978 | Iovine et al. |
| 4,165,367 A | 8/1979 | Chakrabarti |
| 4,957,732 A | 9/1990 | Grollier et al. |
| 5,230,007 A | 7/1993 | Baum |
| 6,190,671 B1 | 2/2001 | Aubert et al. |
| 2010/0075881 A1* | 3/2010 | Tsaur ............ C11D 1/94 510/129 |
| 2013/0156715 A1* | 6/2013 | Hall ............ A61K 8/27 424/70.1 |
| 2013/0296289 A1 | 11/2013 | Hall et al. |

FOREIGN PATENT DOCUMENTS

| EP | 0186507 A2 | 7/1986 |
| EP | 0342834 A1 | 11/1989 |
| FR | 1492597 A | 8/1967 |
| FR | 2077143 A5 | 10/1971 |
| FR | 2393573 A1 | 1/1979 |
| WO | 93/00741 A1 | 1/1993 |
| WO | 94/02158 A1 | 2/1994 |
| WO | 2012022552 A1 | 2/2012 |

OTHER PUBLICATIONS

International Search Report for Application No. PCT/EP2016/080799, dated Mar. 31, 2017.
Porter, M.R., "Handbook of Surfactants," published by Blackie & Son (Glasgow and London), 1991, pp. 116-178.
Mintel: "Medicated Shampoo W-Rinse," Kao, XP002755609, Oct. 1, 2015.
Mintel: "Shampoo," Labach, XP002755608, Oct. 1, 2014.

* cited by examiner

*Primary Examiner* — Robert A Wax
*Assistant Examiner* — Randeep Singh
(74) *Attorney, Agent, or Firm* — The Marbury Law Group, PLLC (57) ABSTRACT

The invention relates to a cosmetic composition which comprises: (i) one or more anionic surfactants, (ii) at least 3.5% by weight of one or more fatty acids, relative to the total weight of the composition, and (iii) one or more antidandruff agents, the anionic surfactant(s)/fatty acid(s) weight ratio being from 0.5 to 3.5. The invention also relates to the use of said composition for washing and conditioning the hair.

13 Claims, 2 Drawing Sheets

COSMETIC COMPOSITION COMPRISING AN ANIONIC SURFACTANT, AT LEAST 3.5% BY WEIGHT OF A FATTY ACID AND AN ANTIDANDRUFF AGENT

CROSS REFERENCE TO RELATED APPLICATIONS

This is a national stage application of PCT/EP2016/080799, filed internationally on Dec. 13, 2016, which claims priority to French Application No. 1562405, filed on Dec. 15, 2015, both of which are incorporated by reference herein in their entireties.

The present invention relates to a cosmetic composition comprising at least one anionic surfactant, at least 3.5% by weight of at least one fatty acid in a particular anionic surfactant(s)/fatty acid(s) weight ratio, and at least one antidandruff agent, to its use for the cosmetic treatment of keratin fibres and to a cosmetic treatment process using this composition.

In the field of hair hygiene, dandruff problems affect up to 50% of the population worldwide. The appearance of dandruff is an inconvenience, in particular from an aesthetic viewpoint.

Care products exist which make it possible to limit these phenomena. However, these products are generally unstable and are not always sufficiently effective.

In particular, these products may have particle flocculation or sedimentation problems.

Specifically, most of the antidandruff agents used are hydrophobic fillers. The incorporation and the stability of these antidandruff agents may prove difficult for a person skilled in the art for two reasons: the placing of the antidandruff fillers in suspension, and the formation of aggregates which may reduce the specific surface area of the active agent and thus potentially its efficacy. The addition of suspensive polymers in high concentration is often necessary to stabilize the antidandruff active agents in the formulation, but this may have a negative impact on the foam abundance and the price of the formulations.

There is thus a need to develop compositions for the cosmetic treatment of keratin fibres that can overcome the drawbacks mentioned above, and that can achieve good stability and good working qualities such as easy and homogeneous distribution and good foam quality, and also very good cosmetic properties in terms of feel, smoothness, suppleness and disentangling.

The Applicant has now discovered that a combination of at least one anionic surfactant, at least 3.5% by weight, relative to the total weight of the composition, of at least one fatty acid, and of at least one antidandruff agent, the anionic surfactant(s)/fatty acid(s) weight ratio being from 0.5 to 3.5, makes it possible to achieve the objectives outlined above.

This combination makes it possible to obtain surfactants arranged in lamellar structured phases. These structured phases have remarkable rheological characteristics that lead to the production of suspensive properties and a capacity for stabilizing hydrophobic fillers of antidandruff active agent type. Oil-mediated vectorization of fillers of this type has an additional advantage in terms of the dispersing and formulating of these active agents.

One subject of the invention is thus a cosmetic composition comprising:
(i) one or more anionic surfactants,
(ii) at least 3.5% by weight of one or more fatty acids, relative to the total weight of the composition, and
(iii) one or more antidandruff agents,
the anionic surfactant(s)/fatty acid(s) weight ratio being from 0.5 to 3.5.

This composition is in the form of structured phases that are stable, and makes it possible to obtain good foam volume. In addition, it leads to the production of excellent cosmetic properties, most particularly of the suppleness and smooth feel of the hair; it also makes it possible to improve the feel and the disentangling, especially on hair that has been sensitized, in particular by bleaching treatments.

A subject of the present invention is also a cosmetic treatment process, and more particularly a process for washing and conditioning keratin fibres, in particular human keratin fibres, such as the hair, comprising the use of the composition according to the invention.

Another subject of the invention consists of the use of a composition according to the invention for the cosmetic treatment of keratin fibres, in particular human keratin fibres, and more particularly the hair.

Other subjects, characteristics, aspects and advantages of the invention will emerge even more clearly on reading the description and the examples that follow.

The FIG. 1 describes the stability of two compositions with or without lauric acid.

The FIG. 2 describes the stability of two compositions according to the ratio between anionic surfactants/fatty acids.

In the text hereinbelow, unless otherwise indicated, the limits of a range of values are included in that range, especially in the expressions "between" and "ranging from . . . to . . . ".

The expression "at least one" used in the present description is equivalent to the expression "one or more".

For the purposes of the present invention, the term "stable composition" more particularly means a composition which does not show any particle flocculation or sedimentation, or any phase separation or decantation, when it is stored at a given temperature, especially between 10 and 50° C. for a period ranging from a few days to 2 months.

According to the invention, the cosmetic composition comprises:
(i) one or more anionic surfactants,
(ii) at least 3.5% by weight of one or more fatty acids, relative to the total weight of the composition, and
(iii) one or more antidandruff agents,
the anionic surfactant(s)/fatty acid(s) weight ratio being from 0.5 to 3.5.

The term "anionic surfactant" means a surfactant comprising, as ionic or ionizable groups, only anionic groups. These anionic groups are preferably chosen from the following groups: —$CO_2H$, —$CO_2^-$, —$SO_3H$, —$SO_3^-$, —$OSO_3H$, —$OSO_3^-$, —$H_2PO_3$, —$HPO_3^-$, —$PO_3^{2-}$, —$H_2PO_2$, —$HPO_2^-$, —$PO_2^{2-}$, —POH or —$PO^-$.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N-acyltaurates, salts of alkyl monoesters of polyglycoside-polycarboxylic acids, acyl lactylates, D-galactoside-uronic acid salts, alkyl ether carboxylic acid salts, alkylaryl ether carboxylic acid salts, alkylamido ether carboxylic acid salts; and the corresponding non-salified forms of all these compounds; the alkyl and acyl groups of all these compounds comprising from 6 to 40 carbon atoms and preferably from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in the form of salts, they may be chosen from alkali metal salts such as the sodium or potassium salt and preferably the sodium salt, the ammonium salts, the amine salts and in particular the amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

In a first variant, the anionic surfactants may be chosen from ($C_6$-$C_{24}$)alkyl sulfates, ($C_6$-$C_{24}$)alkyl ether sulfates comprising from 1 to 50 ethylene oxide units, especially in the form of alkali metal, ammonium, amino alcohol and alkaline-earth metal salts, or a mixture of these compounds.

Even better still, ($C_{12}$-$C_{20}$)alkyl sulfates, ($C_{12}$-$C_{20}$)alkyl ether sulfates comprising from 1 to 20 ethylene oxide units, in particular in the form of alkali metal, ammonium, amino alcohol and alkaline-earth metal salts, or a mixture of these compounds, are preferred in this variant. Better still, sodium or ammonium lauryl sulfate and sodium lauryl ether sulfate are preferred.

In a second variant, the anionic surfactants may be chosen from surfactants comprising anionic groups chosen from —C(O)OH, —C(O)O$^-$, —SO$_3$H or —S(O)$_2$O$^-$, such as alkylsulfonates, olefin sulfonates, alkylamide sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates, N-acyltaurates, acyl lactylates or N-acylglycinates, the alkyl and acyl groups of all these compounds comprising from 6 to 40 carbon atoms and preferably from 6 to 24 carbon atoms.

Most particularly, use may be made of ($C_{6-40}$ acyl)glutamates, better still ($C_{6-24}$ acyl)glutamates, for instance the disodium cocoyl glutamate provided under the trade name Plantapon ACG LC by the company BASF, or ($C_{6-40}$ acyl)isethionates and better still ($C_{6-24}$ acyl)isethionates, for instance the sodium lauroyl methyl isethionate sold by the company Innospec under the trade name Iselux LQ-CLR-SB.

The anionic surfactant(s) are preferably present in a total amount ranging from 0.1% to 40% by weight, preferably ranging from 1% to 30% by weight, better still from 10% to 20% by weight and preferentially from 11% to 15% by weight, relative to the total weight of the composition.

The cosmetic composition comprises one or more fatty acids as other essential ingredient.

For the purposes of the present invention, the term "fatty acid" means an acid comprising at least one linear or branched, saturated or unsaturated hydrocarbon-based chain, such as alkyl or alkenyl, comprising at least 8 carbon atoms, preferably from 8 to 30 carbon atoms, and better still from 10 to 22 carbon atoms.

They preferably have the structure R—COOH in which R denotes a linear or branched $C_7$-$C_{31}$, preferably $C_9$-$C_{21}$, better still $C_9$-$C_{17}$ alkyl or alkenyl group.

As examples of fatty acids that may be used in the present invention, mention may be made especially of lauric acid, oleic acid, linoleic acid, linolenic acid, undecylenic acid, isocetylic acid, isostearylic acid, cetylic acid, stearylic acid and cetylstearylic acid, and mixtures thereof.

Preferably, the fatty acid is chosen from linear fatty acids, better still from saturated linear $C_{10}$-$C_{22}$ and especially $C_{10}$-$C_{18}$ fatty acids.

Lauric acid may preferentially be used.

The fatty acid(s) are preferably present in a total amount ranging from 3.5% to 30% by weight, preferably from 3.5% to 20% by weight, better still from 3.75% to 15% by weight and even better still from 4% to 8% by weight relative to the total weight of the composition.

Preferably, the composition has an anionic surfactant(s)/fatty acid(s) weight ratio ranging from 1 to 3 and more preferentially from 1.5 to 3.

According to the invention, the composition comprises one or more antidandruff agents.

The antidandruff agents that may be used according to the invention are especially chosen from the families (1) to (10) below:

1) pyridinethione salts, in particular the calcium, magnesium, barium, strontium, zinc, cadmium, tin and zirconium salts. The zinc salt of pyridinethione is particularly preferred.

The zinc salt of pyridinethione is sold in particular under the name Omadine zinc by the company Arch Personal Care;

2) 1-hydroxy-2-pyrrolidone derivatives represented especially by formula (I);

in which $R_9$ represents an alkyl group containing from 1 to 17 carbon atoms, an alkenyl group containing from 2 to 17 carbon atoms, a cycloalkyl group containing from 5 to 8 carbon atoms, a bicycloalkyl group containing from 7 to 9 carbon atoms; a cycloalkylalkyl group, an aryl group, an aralkyl group with an alkyl containing from 1 to 4 carbon atoms, an arylalkenyl group with an alkenyl containing from 2 to 4 carbon atoms, aryloxyalkyl or arylmercaptoalkyl with an alkyl containing from 1 to 4 carbon atoms, a furylalkenyl group with an alkenyl or a furyl containing from 2 to 4 carbon atoms, an alkoxy group containing from 1 to 4 carbon atoms, a nitro group, a cyano group or a halogen atom.

$R_{10}$ represents a hydrogen atom, a $C_1$-$C_4$ alkyl group, a $C_2$-$C_4$ alkenyl group, a halogen atom, a phenyl group or a benzyl group;

Y represents an organic base, an alkali metal or alkaline-earth metal ion or an ammonium ion.

Examples of compounds of formula (I) include 1-hydroxy-4-methyl-2-pyridone, 1-hydroxy-6-methyl-2-pyridone, 1-hydroxy-4,6-dimethyl-2-pyridone, 1-hydroxy-4- methyl-6-(2,4,4-trimethylpentyl)-2-pyridone, 1-hydroxy-4-methyl-6-cyclohexyl-2-pyridone, 1-hydroxy-4-methyl-6-(methylcyclohexyl)-2-pyridone, 1-hydroxy-4-methyl-6-(2-bicyclo[2,2,1]heptyl)-2-pyridone, 1-hydroxy-4-methyl-6-(4-methylphenyl)-2-pyridone, 1-hydroxy-4-methyl-6-[1-(4-nitrophenoxy)butyl]-2-pyridone, 1-hydroxy-4-methyl-6-(4-cyanophenoxymethyl)-2-pyridone, 1-hydroxy-4-methyl-6-(phenylsulfonylmethyl)-2-pyridone and 1-hydroxy-4-methyl-6-(4-bromobenzyl)-2-pyridone.

The compounds of formula (I) may be used in the form of salts with organic or mineral bases.

Examples of organic bases are especially alkanolamines of low molecular weight such as ethanolamine, diethanolamine, N-ethylethanolamine, triethanolamine, diethylaminoethanol and 2-amino-2-methylpropanediol; non-volatile bases such as ethylenediamine, hexamethylenediamine, cyclohexylamine, benzylamine and N-methylpiperazine; quaternary ammonium hydroxides, such as trimethylbenzylammonium hydroxide; guanidine and derivatives thereof, and particularly alkyl derivatives thereof. Examples of mineral bases are especially salts of alkali metals, e.g. sodium or potassium; ammonium salts, salts of alkaline-earth metals, such as magnesium or calcium; salts of di-, tri- or tetravalent cationic metals, e.g. zinc, aluminium or zirconium.

Alkanolamines, ethylenediamine and mineral bases such as alkali metal salts are preferred.

A compound of formula (I) that is particularly preferred is the one for which:

$R_9$ denotes the group $R_{10}$ denotes a methyl group, and
$X^+$ denotes $N^+H_3CH_2CH_2OH$.

This compound is sold, for example, under the name Octopirox (1-hydroxy-4-methyl-6-(2,4,4-trimethylpentyl)-2-pyridone, monoethanolamine salt) by the company Hoechst;

3) 2,2'-dithiobis(pyridine N-oxide) of formula (II):

The compounds of formula (II) may be introduced into the compositions in the form of mineral salts. An example of a mineral salt is magnesium sulfate;

4) the trihalocarbamides especially of formula (III) below:

in which Z represents a halogen atom such as chlorine or a $C_1$-$C_4$ trihaloalkyl group such as $CF_3$;

5) triclosan, represented by formula (IV):

6) azole compounds such as climbazole, ketoconazole, clotrimazole, econazole, isoconazole and miconazole;

7) antifungal polymers such as amphotericin B or nystatin;

8) selenium sulfides, in particular those of formula $S_xSe_{8-x}$, x ranging from 1 to 7;

9) extracts of one or more non-photosynthetic, non-fruiting filamentous bacteria.

The bacterial extracts that may be used according to the invention will be chosen from non-photosynthetic, non-fruiting filamentous bacteria as defined according to the classification in Bergey's Manual of Systemic Bacteriology, volume 3, section 23, 9th edition 1989.

Among the bacteria that may be used, mention will be made more particularly of bacteria belonging to the order Beggiatoales, and especially bacteria belonging to the genus *Beggiotoa*, for instance various strains of *Beggiotoa alba*. According to the definition, *B. alba* corresponds to the former names *Beggiotoa arachnoidea*, *B. gigantea*, *B. leptomiformis*, *B. minima* and *B. mirabilis* of Bergey's manual, 8th edition. Mention may moreover be made of bacteria belonging to the genus *Vitreoscilla*, which is known to be close to and often difficult to distinguish from the genus *Beggiatoa*. The bacteria that have just been defined, and several of which have been described, generally have an aquatic habitat, and may be found in particular in spring water sources.

Among the bacteria that may be used, mention may be made, for example, of *Vitreoscilla beggiatoides* (ATCC 43181) and *Beggiatoa alba* (ATCC33555).

Preferentially, according to the invention, the use of the extract of *Vitreoscilla filiformis*, in particular the strain ATCC 15551, metabolites thereof and fractions thereof, are claimed.

Moreover, it is known that culturing non-photosynthetic, non-fruiting filamentous bacteria is relatively difficult, as is the production of pure cultures. Use will preferentially be made of the culture described in patent application WO 94/02158.

The term "extract of non-photosynthetic, non-fruiting filamentous bacteria" means not only the culture supernatant but also the biomass obtained after culturing said bacteria, the envelopes or envelope fractions, or the extracts of the biomass obtained by treating this biomass.

To prepare the extract according to the invention, said bacteria can be cultured and then separated from the biomass obtained, for example by filtration, centrifugation, coagulation and/or lyophilization.

The extracts that may be used may in particular be prepared according to the process described in patent application WO-A-93/00741. Thus, after culturing, the bacteria are concentrated by centrifugation. The biomass obtained is autoclaved. This biomass may be lyophilized to constitute what is known as the lyophilized extract. Any lyophilization method known to those skilled in the art may be used to prepare this extract.

The supernatant fraction of this biomass may also be filtered in a sterile container to remove the particles in suspension.

The terms "envelopes" and "envelope fractions" refer herein to the bacterial wall and possibly the subjacent membranes;

10) other antidandruff agents are sulfur in its various forms, cadmium sulfide, allantoin, coal or wood tars and derivatives thereof, in particular cade oil, salicylic acid, undecylenic acid, fumaric acid, ellagic acid, ellagic acid tannins, and allylamines such as terbinafine.

Even more preferentially, the antidandruff agents that may be used in the invention are chosen from pyridinethione salts, 1-hydroxy-2-pyrrolidone derivatives, 2,2'-dithiobis (pyridine N-oxide) and selenium sulfides, and mixtures thereof.

Pyridinethione zinc, (1-hydroxy-4-methyl-6-(2,4,4-trimethylpentyl)-2-pyridone and salts thereof and selenium sulfides are particularly preferred.

The antidandruff agent(s) are present in the composition according to the invention in preferential proportions ranging from 0.01% to 20% by weight, more preferentially from 0.1% to 10% by weight and better still from 0.2% to 5% by weight, relative to the total weight of the composition.

The composition according to the invention may also comprise one or more amphoteric or zwitterionic surfactants.

They may especially be derivatives of optionally quaternized secondary or tertiary aliphatic amines containing at least one anionic group, such as, for example, a carboxylate, sulfonate, sulfate, phosphate or phosphonate group, and in which the aliphatic group or at least one of the aliphatic groups is a linear or branched chain comprising from 8 to 22 carbon atoms.

Mention may be made in particular of $(C_8-C_{20})$alkylbetaines, sulfobetaines, $(C_8-C_{20})$alkylamido$(C_1-C_6)$alkylbetaines such as cocamidopropylbetaine, and $(C_8-C_{20})$alkylamido$(C_1-C_6)$alkylsulfobetaines.

Mention may also be made, among the derivatives of optionally quaternized secondary or tertiary aliphatic amines capable of being employed, of the products with respective structures (V) and (VI) below:

$$R_a\text{—CONHCH}_2\text{CH}_2\text{—N}^+(R_b)(R_c)(\text{CH}_2\text{COO}^-) \quad (V)$$

in which:

$R_a$ represents a $C_{10}$-$C_{30}$ alkyl or alkenyl group derived from an acid $R_a$—COOH preferably present in hydrolysed coconut oil, or a heptyl, nonyl or undecyl group, $R_b$ represents a β-hydroxyethyl group, and $R_c$ represents a carboxymethyl group;

$$R_{a'}\text{—CONHCH}_2\text{CH}_2\text{—N(B)(B')} \quad (VI)$$

in which:

B represents —CH$_2$CH$_2$OX',

X' represents the group —CH$_2$—COOH, CH$_2$—COOZ', —CH$_2$CH$_2$—COOH or —CH$_2$CH$_2$—COOZ', or a hydrogen atom, B' represents —(CH$_2$)$_z$—Y', with z=1 or 2, Y' represents —COOH, —COOZ', or the group —CH$_2$—CHOH—SO$_3$H or —CH$_2$—CHOH—SO$_3$Z',

Z' represents an ion derived from an alkali or alkaline-earth metal, such as sodium, potassium or magnesium; an ammonium ion; or an ion derived from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane, $R_{a'}$ represents a $C_{10}$-$C_{30}$ alkyl or alkenyl group of an acid $R_{a'}$—COOH preferably present in coconut oil or in hydrolysed linseed oil, an alkyl group, in particular of $C_{17}$ and its iso form, or an unsaturated $C_{17}$ group.

These compounds are also classified in the CTFA dictionary, 5th edition, 1993, under the names disodium co coamphodiacetate, disodium lauroamphodiacetate, disodium caprylamphodiacetate, disodium capryloamphodiacetate, disodium co coamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (VIbis):

$$R_{a''}\text{—NH—CH(Y'')—(CH}_2\text{)}_n\text{—C(O)—NH—(CH}_2\text{)}_{n'}\text{—N(R}_d\text{)(R}_e\text{)} \quad (VIbis)$$

in which formula:

Y'' represents the group —C(O)OH, —C(O)OZ'', —CH$_2$—CH(OH)—SO$_3$H or the group —CH$_2$—CH(OH)—SO$_3$—Z'';

$R_d$ and $R_e$, independently of each other, represent a $C_1$-$C_4$ alkyl or hydroxyalkyl group;

Z'' represents a cationic counterion derived from an alkali metal or alkaline-earth metal, such as sodium, an ammonium ion or an ion derived from an organic amine;

$R_{a''}$ represents a $C_{10}$-$C_{30}$ alkyl or alkenyl group of an acid $R_{a''}$—C(O)OH preferably present in coconut oil or in hydrolysed linseed oil;

n and n', independently of each other, denote an integer ranging from 1 to 3.

Among the compounds of formula (VIbis), mention may be made of the compound classified in the CTFA dictionary under the name sodium diethylaminopropyl cocoaspartamide and sold by the company Chimex under the name Chimexane HB.

Preferably, the amphoteric or zwitterionic surfactants are chosen from $(C_8-C_{20})$alkylbetaines, $(C_8-C_{20})$alkylamido $(C_1-C_6)$alkylbetaines and $(C_8-C_{20})$alkyl amphodiacetates, and also mixtures thereof, and better still from $(C_8-C_{20})$ alkylbetaines and $(C_8-C_{20})$alkylamido$(C_1-C_6)$alkylbetaines.

When they are in the composition, the amphoteric or zwitterionic surfactant(s) are preferably present in a total amount ranging from 0.1% to 30% by weight, better still from 1% to 20% by weight and even more preferentially still from 2% to 15% by weight, relative to the total weight of the composition.

The composition according to the invention may also comprise one or more nonionic surfactants.

Examples of nonionic surfactants that may be used in the hair composition according to the invention are described, for example, in the *Handbook of Surfactants* by M. R. Porter, published by Blackie & Son (Glasgow and London), 1991, pp. 116-178. They are in particular chosen from polyethoxylated, polypropoxylated and/or polyglycerolated alcohols, α-diols and $(C_1-C_{20})$alkylphenols, containing at least one fatty chain comprising, for example, from 8 to 18 carbon atoms, the number of ethylene oxide and/or propylene oxide groups possibly ranging in particular from 2 to 50, and the number of glycerol groups possibly ranging in particular from 2 to 30.

Mention may also be made of condensates of ethylene oxide and of propylene oxide with fatty alcohols, polyethoxylated fatty amides preferably having from 2 to 30 ethylene oxide units, polyglycerolated fatty amides comprising on average from 1 to 5 glycerol groups, and in particular from 1.5 to 4, ethoxylated fatty acid esters of sorbitan containing from 2 to 30 ethylene oxide units, fatty acid esters of sucrose, fatty acid esters of polyethylene glycol, ($C_6$-$C_{24}$ alkyl)-mono- or -polyglycosides, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The nonionic surfactants that are particularly preferred are ($C_6$-$C_{24}$ alkyl)-mono- or -polyglycosides, and oxyalkylenated fatty alcohols.

When they are in the composition, the nonionic surfactant(s) are preferably present in a total amount ranging from 0.1% to 30% by weight, better still from 1% to 20% by weight and even more preferentially from 2% to 15% by weight, relative to the total weight of the composition.

Preferably, the cosmetic composition comprises a total amount of anionic, amphoteric, zwitterionic and nonionic surfactants ranging from 1% to 50% by weight, better still from 5% to 40% by weight and even more preferentially from 10% to 30% by weight, relative to the total weight of the composition.

The composition according to the invention may also comprise one or more non-silicone fatty substances, which are preferably liquid, other than the fatty acids according to the invention.

The term "non-silicone fatty substance" means an organic compound that is insoluble in water at ordinary temperature (25° C.) and at atmospheric pressure (760 mmHg) (solubility less than 5% and preferably 1% and even more preferentially 0.1%). They bear in their structure at least one hydrocarbon-based chain comprising at least 6 carbon atoms. In addition, the fatty substances are generally soluble in organic solvents under the same temperature and pressure conditions, for instance chloroform, ethanol, benzene, liquid petroleum jelly or decamethylcyclopentasiloxane.

The term "oil" means a "fatty substance" that is liquid at room temperature (25° C.) and at atmospheric pressure (760 mmHg or $1.013 \times 10^5$ Pa).

The term "non-silicone oil" means an oil not containing any silicon (Si) atoms.

More particularly, the fatty substances are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides, non-silicone waxes other than solid fatty alcohols and than solid synthetic esters, and mixtures thereof.

It is recalled that, for the purposes of the invention, fatty alcohols, esters and acids more particularly bear at least one linear or branched, saturated or unsaturated hydrocarbon-based group comprising 6 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

The linear or branched hydrocarbons of mineral or synthetic origin containing more than 16 carbon atoms are preferably chosen from liquid paraffins, liquid petroleum jelly, polydecenes and hydrogenated polyisobutene such as Parleam®, and mixtures thereof.

As regards the $C_6$-$C_{16}$ lower alkanes, they are linear or branched, or possibly cyclic.

Examples that may be mentioned include hexane, cyclohexane, undecane, dodecane, tridecane or isoparaffins, such as isohexadecane, isodecane or isododecane, and mixtures thereof.

A hydrocarbon-based oil of animal origin that may be mentioned is perhydrosqualene.

The triglycerides of plant or synthetic origin are preferably chosen from liquid fatty acid triglycerides containing from 6 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stéarineries Dubois or those sold under the names Miglyol® 810, 812 and 818 by the company Dynamit Nobel, and mixtures thereof.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols comprising from 8 to 30 carbon atoms. Examples that may be mentioned include cetyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

As regards the esters of fatty acids and/or of fatty alcohols other than the triglycerides mentioned above and plant waxes, mention may be made in particular of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar and fatty acid esters may be chosen in particular from the group comprising the esters or mixtures of sugar esters described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleate or dioleate, stearate, behenate, oleopalmitate, linoleate, linolenate or oleostearate.

An example that may be mentioned is the product sold under the name Glucate® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% di-triester-polyester;

the sucrose mono-dipalmito-stearate sold by the company Goldschmidt under the name Tegosoft® PSE.

The non-silicone wax(es) other than solid fatty alcohols and solid synthetic esters are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy raw materials that may be used according to the invention are in particular marine waxes, such as the wax sold by the company Sophim under the reference M82, polyethylene waxes or polyolefin waxes in general.

The fatty substance(s) do not comprise any $C_2$-$C_3$ oxyalkylene units. Preferably, they do not contain any glycerol units.

More particularly, the fatty substances are chosen from compounds that are liquid or pasty at room temperature and at atmospheric pressure.

Preferably, the fatty substance is a compound that is liquid at a temperature of 25° C. and at atmospheric pressure, or oil.

Preferably, the non-silicone fatty substance(s) other than fatty acids are chosen from oils of plant origin, fatty esters, and mixtures thereof, better still from oils of plant origin and liquid fatty esters, and mixtures thereof.

Even more preferentially, the non-silicone fatty substance(s) other than fatty acids are chosen from oils of plant origin, better still from sunflower oil and avocado oil.

When they are in the composition, the non-silicone fatty substance(s) are preferably present in an amount ranging from 0.1% to 30% by weight, better still from 0.5% to 20% by weight and even more preferentially from 1% to 10% by weight, relative to the total weight of the composition.

The composition according to the invention may also comprise one or more cationic polymers.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) Homopolymers or copolymers derived from acrylic or methacrylic esters or amides and comprising at least one of the units of the following formulae:

in which:

R$_3$, which may be identical or different, denote a hydrogen atom or a CH$_3$ group;

A, which may be identical or different, represent a linear or branched divalent alkyl group of 1 to 6 carbon atoms, preferably 2 or 3 carbon atoms, or a hydroxyalkyl group of 1 to 4 carbon atoms;

R$_4$, R$_5$ and R$_6$, which may be identical or different, represent an alkyl group containing from 1 to 18 carbon atoms or a benzyl group, and preferably an alkyl group containing from 1 to 6 carbon atoms;

R$_1$ and R$_2$, which may be identical or different, represent a hydrogen atom or an alkyl group containing from 1 to 6 carbon atoms, and preferably methyl or ethyl;

X denotes an anion derived from a mineral or organic acid, such as a methosulfate anion or a halide such as chloride or bromide.

The copolymers of family (1) may also contain one or more units derived from comonomers which may be chosen from the family of acrylamides, methacrylamides, diacetone acrylamides, acrylamides and methacrylamides substituted on the nitrogen with C$_1$-C$_4$ alkyls, acrylic or methacrylic acids or esters thereof, vinyllactams such as vinylpyrrolidone or vinylcaprolactam, and vinyl esters.

Among these copolymers of family (1), mention may be made of:

copolymers of acrylamide and of dimethylaminoethyl methacrylate quaternized with dimethyl sulfate or with a dimethyl halide, such as that sold under the name Hercofloc by the company Hercules, copolymers of acrylamide and of methacryloyloxyethyltrimethylammonium chloride, such as the product sold under the name Bina Quat P 100 by the company Ciba Geigy, the copolymer of acrylamide and of methacryloyloxyethyltrimethylammonium methosulfate, such as that sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers, such as the product sold under the name Styleze CC 10 by ISP, quaternized vinylpyrrolidone/dimethylaminopropylmethacrylamide copolymers such as the product sold under the name Gafquat HS 100 by the company ISP, preferably crosslinked polymers of methacryloyloxy(C$_1$-C$_4$)alkyl tri(C$_1$-C$_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by Ciba.

(2) Cationic polysaccharides, in particular cationic celluloses and cationic galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR 1 492 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, a chloride). Such products are in particular sold under the names Jaguar C13 S, Jaguar C 15, Jaguar C 17 and Jaguar C162 by the company Rhodia.

(3) Polymers composed of piperazinyl units and of divalent alkylene or hydroxyalkylene groups containing linear or branched chains, optionally interrupted with oxygen, sulfur or nitrogen atoms or with aromatic or heterocyclic rings, and also the oxidation and/or quaternization products of these polymers.

(4) Water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) Polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1. Polymers of this type are sold in particular under the name Hercosett 57 by Hercules Inc. or else under the name PD 170 or Delsette 101 by Hercules in the case of the adipic acid/epoxypropyl/diethylenetriamine copolymer.

(7) Cyclopolymers of alkyldiallylamine or of dialkyldiallylammonium, such as the homopolymers or copolymers comprising, as main constituent of the chain, units corresponding to formula (PI) or (PII):

in which
k and t are equal to 0 or 1, the sum k+t being equal to 1;
$R_{12}$ denotes a hydrogen atom or a methyl group;
$R_{10}$ and $R_{11}$, independently of each other, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidyl or morpholinyl; $R_{10}$ and $R_{11}$, independently of each other, preferably denote an alkyl group containing from 1 to 4 carbon atoms;
$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco (and homologues thereof of low weight-average molar masses) and the copolymers of diallyldimethylammonium salts (for example chloride) and of acrylamide, sold in particular under the name Merquat 550 or Merquat 7SPR.

(8) Quaternary diammonium polymers comprising repeating units of formula:

(PIII)

in which:
$R_{13}$, $R_{14}$, $R_{15}$ and $R_{16}$, which may be identical or different, represent aliphatic, alicyclic or arylaliphatic groups comprising from 1 to 20 carbon atoms or $C_{1-4}$ hydroxyalkylaliphatic groups, or else $R_{13}$, $R_{14}$, $R_{15}$ and $R_{16}$, together or separately, form, with the nitrogen atoms to which they are attached, heterocycles optionally comprising a second heteroatom other than nitrogen, or else $R_{13}$, $R_{14}$, $R_{15}$ and $R_{16}$ represent a linear or branched $C_1$-$C_6$ alkyl group substituted with a nitrile, ester, acyl, amide or —CO—O—$R_{17}$-D or —CO—NH—$R_{17}$-D group, where $R_{17}$ is an alkylene and D a quaternary ammonium group;

$A_1$ and $B_1$ represent divalent polymethylene groups comprising from 2 to 20 carbon atoms which may be linear or branched, and saturated or unsaturated, and which may contain, linked to or inserted in the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

it being understood that $A_1$, $R_{13}$ and $R_{15}$ can form, with the two nitrogen atoms to which they are attached, a piperazine ring.

In addition, if $A_1$ denotes a saturated or unsaturated and linear or branched alkylene or hydroxyalkylene group, $B_1$ can also denote a $(CH_2)_n$—CO-D-OC—$(CH_2)_n$— group in which D denotes:

a) a glycol residue of formula —O—Z—O—, in which Z denotes a linear or branched hydrocarbon-based group, or a group corresponding to one of the following formulae: —$(CH_2$—$CH_2$—$O)_x$—$CH_2$—$CH_2$— and —[$CH_2$—CH($CH_3$)—O]$_y$—$CH_2$—CH($CH_3$)—, where x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, in which Y denotes a linear or branched hydrocarbon-based group, or alternatively the divalent group —CH$_2$—CH$_2$—S—S—CH$_2$—CH$_2$—;

d) a ureylene group of formula: —NH—CO—NH—.

Preferably, X$^-$ is an anion, such as chloride or bromide. These polymers have a number-average molar mass (Mn) generally of between 1000 and 100 000.

Mention may be made more particularly of polymers that are composed of repeating units corresponding to the formula:

(PIV)

in which R$_1$, R$_2$, R$_3$ and R$_4$, which may be identical or different, denote an alkyl or hydroxyalkyl group containing from 1 to 4 carbon atoms approximately, n and p are integers ranging from 2 to 20 approximately, and X$^-$ is an anion derived from a mineral or organic acid.

A compound of formula (PIV) that is particularly preferred is the one for which R$_1$, R$_2$, R$_3$ and R$_4$ represent a methyl group and n=3, p=6 and X=Cl, which is known as Hexadimethrine chloride according to the INCI (CTFA) nomenclature.

(9) Polyquaternary ammonium polymers comprising units of formula (PV):

in which:

R$_{18}$, R$_{19}$, R$_{20}$ and R$_{21}$, which may be identical or different, represent a hydrogen atom or a methyl, ethyl, propyl, β-hydroxyethyl, β-hydroxypropyl or —CH$_2$CH$_2$(OCH$_2$CH$_2$)$_p$OH group, where p is equal to 0 or to an integer of between 1 and 6, with the proviso that R$_{18}$, R$_{19}$, R$_{20}$ and R$_{21}$ do not simultaneously represent a hydrogen atom, r and s, which may be identical or different, are integers between 1 and 6, q is equal to 0 or to an integer between 1 and 34, X$^-$ denotes an anion such as a halide, A denotes a radical of a dihalide or preferably represents —CH$_2$—CH$_2$—O—CH$_2$—CH$_2$—.

Examples that may be mentioned include the products Mirapol® A 15, Mirapol® AD1, Mirapol® AZ1 and Mirapol® 175 sold by the company Miranol.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

(A)

(b) optionally one or more units corresponding to formula (B) below:

(B)

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to the formula (A) and from 0 mol % to 95 mol % of units corresponding to the formula (B), preferably from 10 mol % to 100 mol % of units corresponding to the formula (A) and from 0 mol % to 90 mol % of units corresponding to the formula (B).

These polymers may be obtained, for example, by partial hydrolysis of polyvinylformamide. This hydrolysis may be performed in acidic or basic medium.

The weight-average molecular mass of said polymer, measured by light scattering, may range from 1000 to 3 000 000 g/mol, preferably from 10 000 to 1 000 000 and more particularly from 100 000 to 500 000 g/mol.

The cationic charge density of these polymers may range from 2 to 20 meq/g, preferably from 2.5 to 15 meq/g and more particularly from 3.5 to 10 meq/g.

The polymers comprising units of formula (A) and optionally units of formula (B) are sold in particular under the Lupamin name by BASF, such as, for example, in a non-limiting way, the products provided under the names Lupamin 9095, Lupamin 5095, Lupamin 1095, Lupamin 9030 (or Luviquat 9030) and Lupamin 9010.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from cationic polysaccharides, such as those described in family (2) above.

Among the cationic polymers mentioned above, use may preferably be made of cationic polysaccharides, especially cationic celluloses and cationic galactomannan gums, and in particular quaternary cellulose ether derivatives comprising quaternary ammonium groups, in particular among quaternary ammoniums of hydroxyethylcellulose that has reacted with an epoxide substituted with a trimethylammonium group, having the INCI name Polyquaternium-10, such as the products sold under the name JR 400 by the company Amerchol or Celquat SC-240C by the company Akzo Nobel.

When they are in the composition, the cationic polymer(s), preferably the cationic polysaccharide(s), are especially present in a total amount ranging from 0.01% to 10% by weight, better still from 0.05% to 5% by weight and even more preferentially from 0.1% to 2% by weight, relative to the total weight of the composition.

The composition according to the invention also comprises one or more silicones.

They may be solid or liquid, volatile or non-volatile, and amine-based or non-amine-based.

As silicones that may be used, mention may be made, alone or as a mixture, of polydialkylsiloxanes and especially polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, especially polydiphenylsiloxanes, and polyalkylarylsiloxanes, functionalized with the organofunctional groups mentioned previously.

Among the organomodified silicones, mention may be made of organopolysiloxanes comprising:
  polyoxyethylene and/or polyoxypropylene groups optionally comprising $C_6$-$C_{24}$ alkyl groups, such as dimethicone copolyols, and especially those sold by the company Dow Corning under the name DC 1248 or the oils Silwet® L 722, L 7500, L 77 and L 711 from the company Union Carbide; or alternatively (C12)alkylmethicone copolyols, and especially those sold by the company Dow Corning under the name Q2 5200;
  substituted or unsubstituted amine groups, in particular C1-C4 aminoalkyl groups; mention may be made of the products sold under the name GP4 Silicone Fluid and GP7100 by the company Genesee, or under the names Q2-8220 and DC929 or DC939 by the company Dow Corning;
  thiol groups, such as the products sold under the names GP 72 A and GP 71 from Genesee;
  alkoxylated groups, such as the product sold under the name Silicone Copolymer F-755 by SWS Silicones and Abil Wax® 2428, 2434 and 2440 by the company Goldschmidt;
  hydroxylated groups, for instance polyorganosiloxanes bearing a hydroxyalkyl function;
  acyloxyalkyl groups, such as the polyorganosiloxanes described in U.S. Pat. No. 4,957,732;
  anionic groups of the carboxylic acid type, as described, for example, in EP 186 507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;
  hydroxyacylamine groups, such as the polyorganosiloxanes described in patent application EP 342 834; mention may be made, for example, of the product Q2-8413 from the company Dow Corning.

The polydialkylsiloxanes may be chosen mainly from polydimethylsiloxanes bearing trimethylsilyl end groups.

Among these polydialkylsiloxanes, mention may be made of the following commercial products:
  the Silbione® oils of the 47 and 70 047 series or the Mirasil® oils sold by Rhodia, such as, for example, the oil 70 047 V 500 000;
  the oils of the Mirasil® series sold by the company Rhodia;
  the oils of the 200 series from the company Dow Corning, such as DC200 with a viscosity of 60 000 mm$^2$/s;
  the Viscasil® oils from General Electric and certain oils of the SF series (SF 96, SF 18) from General Electric.

Mention may also be made of polydimethylsiloxanes having dimethylsilanol end groups known as dimethiconol (CTFA), such as the oils in the 48 series from Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that may be used more particularly in accordance with the invention are mixtures such as:
  mixtures formed from a hydroxy-terminated polydimethylsiloxane or dimethiconol (CTFA), and from a cyclic polydimethylsiloxane, also known as cyclomethicone (CTFA), such as the product Q2 1401 sold by the company Dow Corning.

The polyalkylarylsiloxanes are chosen particularly from linear and/or branched polydimethyl/methylphenylsiloxanes and polydimethyl/diphenylsiloxanes preferably with a viscosity ranging from $1 \times 10^{-5}$ to $5 \times 10^{-2}$ m$^2$/s at 25° C.

Among these polyalkylarylsiloxanes, mention may be made of the products sold under the following names:
  the Silbione® oils of the 70 641 series from Rhodia;
  oils of the Rhodorsil® 70 633 and 763 series from Rhodia;
  the oil Dow Corning 556 Cosmetic Grade Fluid from Dow Corning;
  the silicones of the PK series from Bayer, such as the product PK20;
  the silicones of the PN and PH series from Bayer, such as the products PN1000 and PH1000;
  certain oils of the SF series from General Electric, such as SF 1023, SF 1154, SF 1250 and SF 1265.

Preferably, the composition according to the invention comprises one or more amino silicones.

For the purposes of the present invention, the term "aminosilicone" means any silicone comprising one or more primary, secondary or tertiary amine functions or one or more quaternary ammonium groups.

The aminosilicones that may be used in the cosmetic composition according to the present invention are advantageously chosen, alone or as a mixture, from aminosilicones bearing one or more amine functions, especially primary amines, and aminosilicones bearing one or more non-amidated quaternized amine functions.

According to the present invention, the term "non-amidated silicone" means a silicone that does not comprise any amide functions (—NHC(O)—).

The composition according to the invention may thus comprise in particular one or more aminosilicones chosen from:
  (a) the compounds corresponding to formula (VII) below:

(VII)

in which:

T is a hydrogen atom or a phenyl or hydroxyl (—OH), or $C_1$-$C_8$ alkyl, and preferably methyl, or $C_1$-$C_8$ alkoxy, preferably methoxy, group, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and especially from 49 to 149, and for m to denote a number from 1 to 2000 and especially from 1 to 10, $R^1$ is a monovalent group of formula —$C_qH_{2q}L$ in which q is a number from 2 to 8 and L is an optionally quaternized amine group chosen from the following groups:

—$N(R^2)$—$CH_2$—$CH_2$—$N(R^2)_2$,
—$N(R^2)_2$,
—$N^+(R^2)_3Q^-$,
—$N^+(R^2)(H)_2Q^-$,
—$N^+(R^2)_2HQ^-$,
—$N(R^2)$—$CH_2$—$CH_2$—$N^+(R^2)(H)_2Q^-$, in which $R^2$ may denote a hydrogen atom, a phenyl, benzyl or saturated monovalent hydrocarbon-based group, for example a $C_1$-$C_{20}$ alkyl group, and $Q^-$ represents a halide ion, for example fluoride, chloride, bromide or iodide.

In particular, mention may be made of the amino silicones corresponding to formula (VIII) below:

in which:

R, R' and R", which may be identical or different, denote a $C_1$-$C_4$ alkyl group, preferably $CH_3$, a $C_1$-$C_4$ alkoxy group, preferably methoxy, or OH, A and B represent, independently of each other, a linear or branched $C_2$-$C_8$, preferably $C_3$-$C_6$ alkylene group; A preferably representing a $C_3$-$C_6$ alkylene and B preferably representing a $C_2$-$C_4$ and especially $C_2$ alkylene;

m and n are integers that are dependent on the molecular weight (Mw) of the silicone, and whose sum ranges from 1 to 2000.

According to a first variant of formula (VIII), R, R' and R", which may be identical or different, each represent a $C_1$-$C_4$ alkyl group or a hydroxyl group, A represents a $C_3$ alkylene group and m and n are such that the weight-average molecular mass of the compound is approximately between 5000 and 500 000. The compounds of this type are named "amodimethicone" in the CTFA dictionary.

According to a second variant of formula (VIII), R, R' and R", which may be identical or different, each represent a $C_1$-$C_4$ alkoxy group or a hydroxyl group, at least one of the groups R or R" is a $C_1$-$C_4$ alkoxy group; A represents a $C_3$ alkylene group and B represents a $C_2$-$C_4$ and especially $C_2$ alkylene group; m and n are such that the weight-average molecular mass of the compound is between 2000 and $10^6$; more particularly, n is between 0 and 999 and m is between 1 and 1000, the sum (m+n) being between 1 and 1000.

The hydroxy/alkoxy mole ratio is preferably between 0.2/1 and 0.4/1 and advantageously is equal to 0.3/1.

Mention may be made especially of the product Belsil® ADM 652 sold by the company Wacker.

According to a third variant, R and R", which are different, each represent a $C_1$-$C_4$ alkoxy group or a hydroxyl group, at least one of the groups R and R" being a $C_1$-$C_4$ alkoxy group, R' representing a methyl group, A representing a $C_3$ alkylene group and B representing a $C_2$-$C_4$ and especially $C_2$ alkylene group; m and n are such that the weight-average molecular mass of the compound is between 2000 and 200 000; more particularly, n is between 0 and 999 and m is between 1 and 1000, the sum (m+n) being between 1 and 1000.

The hydroxy/alkoxy mole ratio is preferably between 1/0.8 and 1/1.1 and advantageously is equal to 1/0.95.

Mention may be made especially of the products FinishWR® 1300 and Belsil ADM LOG1 sold by the company Wacker.

According to a fourth variant, R, R" and R' represent a methyl group, A represents a $C_4$ alkylene group and B represents a $C_2$-$C_4$ and especially $C_2$ alkylene group; m and n being integers that are dependent on the molecular weight (Mw) of silicone, and the sum of which ranges from 1 to 2000.

A silicone that is particularly preferred according to this variant is the polymer known in the CTFA dictionary as "trimethylsilyl amodimethicone", corresponding to formula (VIII') below:

in which m and n are integers that are dependent on the molecular weight (Mw) of the silicone, and whose sum ranges from 1 to 2000.

Mention may be made of the product sold under the name Q2-8220 by the company OSI.

(b) the aminosilicones of formula (IX):

in which:

$R_1$, $R_2$, $R_3$ and $R_4$, which may be identical or different, denote a $C_1$-$C_4$ alkyl group or a phenyl group,

$R_5$ denotes a $C_1$-$C_4$ alkyl group or a hydroxyl group, n is an integer ranging from 1 to 5, m is an integer ranging from 1 to 5, and x is chosen such that the amine number is between 0.01 and 1 meq/g.

(c) the silicones corresponding to formula (X) below:

(X)

in which:

$R_5$, which may be identical or different, represent a linear or branched $C_1$-$C_{18}$ alkyl group or a linear or branched $C_2$-$C_{18}$ alkenyl group; preferably a methyl group;

$R_6$ represents a linear or branched divalent $C_1$-$C_{18}$ alkylene group or a linear or branched divalent $C_1$-$C_{18}$, for example $C_1$-$C_8$, alkyleneoxy group linked to the Si via an Si—C bond;

$Q^-$ is an anion such as a halide ion, especially chloride, or an organic acid salt, such as acetate;

r represents a mean statistical value ranging from 2 to 20 and in particular from 2 to 8;

s represents a mean statistical value ranging from 20 to 200 and in particular from 20 to 50.

Mention may be made especially of the product sold by the company Union Carbide under the name Ucar Silicone ALE 56.

(d) the quaternary diammonium silicones of formula (XI):

(XI)

in which:

$R_7$, which may be identical or different, represent a linear or branched $C_1$-$C_{18}$ alkyl group or a linear or branched $C_2$-$C_{18}$ alkenyl group or a hydrocarbon-based ring comprising 5 or 6 carbon atoms; preferably a methyl group;

$R_6$, which may be identical or different, represent a linear or branched divalent $C_1$-$C_{18}$ alkylene group or a linear or branched divalent $C_1$-$C_{18}$, for example $C_1$-$C_8$, alkyleneoxy group linked to the Si via an SiC bond;

$R_8$, which may be identical or different, represent a hydrogen atom, a linear or branched $C_1$-$C_{18}$ alkyl group, a linear or branched $C_2$-$C_{18}$ alkenyl group; or a group —$R_6$—NHCOR$_7$, $R_6$ and $R_7$ being as defined above;

$X^-$ is an anion such as a halide ion, especially chloride, or an organic acid salt, for example acetate;

r represents a mean statistical value ranging from 2 to 200 and in particular from 5 to 100.

A silicone of formula (XI) that is particularly preferred is the one in which all the $R_7$ are methyl groups and all the $R_6$ are $C_1$-$C_8$ and especially $C_2$-$C_4$ alkyleneoxy. In particular, mention may be made of the silicone having the INCI name: Quaternium-80.

As commercial product, mention may be made of the products sold under the name Abil Quat 3272 or Abil Quat 3274 by the company Degussa.

The weight-average molecular mass (Mw) of these silicones may advantageously be determined by gel permeation chromatography (room temperature 25° C., polystyrene standard, µ styragem columns, THF eluent, flow rate of 1 mm/minute, 200 µl of a solution containing 0.5% by weight of silicone in THF are injected, and detection is performed by refractometry and UV-metry).

According to the invention, all these silicones may also be used in the form of emulsions or microemulsions, which may comprise cationic and/or nonionic surfactants.

Mention may thus also be made, as commercial product that may be used according to the invention, of the product sold under the name Dow Corning Q2-7224 by the company Dow Corning, comprising a mixture of trimethylsilyl amodimethicone of formula (XI) defined above, a nonionic surfactant of formula: $C_8H_{17}$—$C_6H_4$—$(OCH_2CH_2)_{40}$—OH, known under the CTFA name Octoxynol-40, a second nonionic surfactant of formula: $C_{12}H_{25}$—$(OCH_2$—$CH_2)_6$—OH, known under the CTFA name Isolaureth-6, and propylene glycol.

Mention may also be made of the product sold under the name Cationic Emulsion DC939 by Dow Corning, which comprises, besides amodimethicone, a cationic surfactant, namely trimethylcetylammonium chloride, and a nonionic surfactant of formula $C_{13}H_{27}$—$(OC_2H_4)_{12}$—OH, known under the CTFA name Trideceth-12.

Mention may also be made of the product sold under the name Wacker-Belsil ADM LOG1 by the company Wacker, which comprises, besides amodimethicone, Trideceth-5 and Trideceth-10.

Mention may also be made of the product sold under the trade name Xiameter MEM 8299 Emulsion by the company Dow Corning.

Preferably, the silicone(s) that may be used in the cosmetic composition according to the invention are chosen from polydialkylsiloxanes, in particular from polydimethylsiloxanes bearing trimethylsilyl end groups, amino silicones, in particular the aminosilicones of formula (VII), and even more particularly from the aminosilicones of formula (VIII) or (VIII').

When they are in the composition, the silicone(s), preferably aminosilicone(s), are present in the composition according to the invention in an amount preferably ranging from 0.01% to 10% by weight, better still from 0.05% to 5% by weight and even more preferentially from 0.1% to 2% by weight, or even between 0.15% and 1.5% by weight, relative to the total weight of the composition.

Preferably, the composition according to the invention is aqueous and comprises water at a concentration preferably ranging from 5% to 98% by weight, in particular from 20% to 95% by weight and better still from 50% to 95% by weight, relative to the total weight of the composition.

The composition may also comprise one or more organic solvents that are liquid at 25° C. and $1.013 \times 10^5$ Pa and which are especially water-soluble, such as $C_1$-$C_7$ alcohols, especially $C_1$-$C_7$ aliphatic or aromatic monoalcohols, and $C_3$-$C_7$ polyols and polyol ethers, which may thus be used alone or as a mixture with water. Advantageously, the organic solvent may be chosen from ethanol and isopropanol, and mixtures thereof.

The pH of the composition, if it is aqueous, is preferably between 3.5 and 9 and in particular between 4.5 and 7.

The pH of these compositions may be adjusted to the desired value by means of basifying agents or acidifying agents that are usually used. Among the basifying agents, examples that may be mentioned include aqueous ammonia, alkanolamines, and mineral or organic hydroxides. Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

The compositions according to the invention may also contain one or more additives chosen from anionic, amphoteric or zwitterionic and nonionic polymers, cationic surfactants, ceramides, pseudo-ceramides, vitamins and provitamins including panthenol, water-soluble and liposoluble sunscreens, nacreous agents and opacifiers, sequestrants, solubilizers, antioxidants, antidandruff agents, anti-seborrhoeic agents, agents for preventing hair loss and/or for promoting hair regrowth, penetrants, fragrances, peptizers and preserving agents, or any other additive conventionally used in the cosmetics field.

These additives may be present in the composition according to the invention in an amount ranging from 0 to 20% by weight, relative to the total weight of the composition.

A person skilled in the art will take care to select these optional additives and amounts thereof so that they do not harm the properties of the compositions of the present invention.

The compositions according to the invention may, in a non-limiting manner, be in the form of conditioning shampoos.

The compositions according to the invention may be prepared in a conventional manner. For example, a hot process may be applied, in which the fatty acid is melted at the start of the preparation and the other essential ingredients of the composition according to the invention are introduced.

The present invention also relates to a cosmetic process for treating, and more particularly for washing and conditioning, keratin fibres, especially human keratin fibres and in particular the hair, which comprises the application to said fibres of an effective amount of a composition as described above, followed by rinsing and drying.

The application may be performed on dry or wet hair.

The leave-on time of the composition on the keratin fibres generally ranges from a few seconds to 60 minutes, better still from 5 seconds to 30 minutes and even better still from 10 seconds to 10 minutes.

This process makes it possible to obtain keratin fibres that have improved cosmetic properties, in terms of feel, smoothness, suppleness and disentangling, more particularly when the composition is applied to hair that has been sensitized by bleaching treatments.

The present invention also relates to the use of the cosmetic composition according to the invention for washing and conditioning the hair.

The invention is illustrated by the following examples.

EXAMPLES

Examples 1-11

The compositions according to the invention were prepared from the ingredients indicated in Tables 1, 2 and 3 below. The amounts indicated are expressed as weight percentages of starting material in unmodified form relative to the total weight of the composition.

TABLE 1

|  | Ex. 1 | Ex. 2 | Ex. 3 |
|---|---|---|---|
| Sodium laureth sulfate containing 70% by weight of AM | — | — | — |
| Ammonium lauryl sulfate containing 26.8% by weight of AM | — | — | 45 |
| Sodium cocoyl isethionate containing 88% by weight of AM | 12.73 | 12.73 | — |
| Cocoyl betaine containing 30% by weight of AM | — | — | 16 |
| Cocamidopropyl betaine containing 38% by weight of AM | 25 | 25 | — |
| Sodium chloride | — | — | 0.5 |
| Lauric acid | 5.6 | 5.6 | 5 |
| Avocado oil | — | 5 | — |
| Polyquaternium-10 (JR400 from Amerchol, containing 91% by weight of AM) | 0.53 (0.48 AM) | — | 0.58 (0.53 AM) |
| Cationic guar gum (Jaguar C13S from Rhodia containing 98.25% by weight of AM) | — | 0.2 (0.196 AM) | — |
| Dimethicone | 1.74 | — | — |
| Fragrance | 0.8 | 0.8 | 0.8 |
| Selenium sulfide | 0.5 | 0.5 | — |
| Zinc pyrithione | — | — | 1 AM |
| Anionic surfactant/lauric acid ratio | 2 | 2 | 2.4 |

AM: active material

TABLE 2

|  | Ex. 4 | Ex. 5 | Ex. 6 |
|---|---|---|---|
| Sodium laureth sulfate containing 70% by weight of AM | — | 1.65 | 3.3 |
| Ammonium lauryl sulfate containing 26.8% by weight of AM | 50 | 44.2 | 26 |
| Cocamidopropyl betaine containing 38% by weight of AM | 13.1 | 18.2 | 10 |
| Sodium chloride | 0.5 | — | — |
| Lauric acid | 5 | 5 | 3.75 |
| Sunflower oil | 2 | — | 2 |
| Butylhydroxytoluene | — | 0.5 | — |
| Polyquaternium-10 (JR400 from Amerchol, containing 91% by weight of AM) | — | — | 0.4 (0.364 AM) |
| Polyquaternium 6 (Merquat 100, containing 40% by weight of AM) | — | 1.25 (0.5 AM) | — |
| Polyquaternium 53 (Merquat 2003, containing 20% by weight of AM) | — | 1.25 (0.25 AM) | — |

TABLE 2-continued

|  | Ex. 4 | Ex. 5 | Ex. 6 |
|---|---|---|---|
| Fragrance | 0.8 | 0.8 | 0.8 |
| Zinc pyrithione | 1 AM | 1 AM | 1 AM |
| Anionic surfactant/lauric acid ratio | 2.6 | 2.6 | 2.5 |

AM: active material

TABLE 3

|  | Ex. 7 | Ex. 8 | Ex. 9 | Ex. 10 | Ex. 11 |
|---|---|---|---|---|---|
| Sodium laureth sulfate containing 70% by weight of AM | 4.96 | 1.65 | 1.65 | 1.65 | — |
| Ammonium lauryl sulfate containing 26.8% by weight of AM | 31.58 | 44.2 | 44.2 | 44.2 | — |
| Sodium cocoyl isethionate containing 88% by weight of AM | — | — | — | — | 12.73 |
| Cocamidopropyl betaine containing 38% by weight of AM | 14.79 | 18.2 | 18.2 | 18.2 | 25 |
| Lauric acid | 5 | 5 | 5 | 5 | 5.6 |
| Avocado oil | 2 | — | — | 2 | 5 |
| Isopropyl myristate | — | — | 2 | — | — |
| Butylhydroxytoluene | — | — | — | 0.5 | — |
| Polyquaternium-10 containing 91% by weight of AM (JR400 from Amerchol) | — | 1 | 1 | 0.4 | 0.4 |
| Cationic guar gum containing 98.25% by weight of AM (Jaguar C13S from Rhodia) | — | — | — | — | 0.2 |
| Aminosilicone containing 15% by weight of AM | — | 1.75 | 1.75 | — | — |
| Carbopol containing 98% by weight of AM | — | — | — | — | 0.15 |
| Fragrance | 0.8 | 0.8 | 0.8 | 0.8 | 0.8 |
| Selenium sulfide | — | — | — | 0.5 | 0.5 |
| Zinc pyrithione | 1 AM | 1 AM | 0.5 AM | — | — |
| Anionic surfactant/lauric acid ratio | 2.4 | 2.6 | 2.6 | 2.6 | 2 |

AM: active material

After preparing the compositions, their stability at 45° C. was studied by leaving them in an oven at this temperature for 2 months. All the formulations were found to be stable.

Examples 12-14

The following compositions were prepared from the ingredients indicated in Table 4 below. The amounts indicated are expressed as weight percentages of starting material in unmodified form relative to the total weight of the composition.

TABLE 4

|  | Ex. 12 | Ex. 13 | Ex. 14 |
|---|---|---|---|
| Sodium cocoyl isethionate containing 88% by weight of AM | 12 | 12 | 12 |
| Cocamidopropyl betaine containing 38% by weight of AM | 25 | 25 | 25 |
| Lauric acid | 0 | 5 | 5 |
| Avocado oil (Persea gratissima (avocado) oil) | — | — | 5 |
| Selenium sulfide | 1 | 1 | 1 |
| NaCl | 1.65 | 1.65 | 1.65 |
| Water qs | 100 | 100 | 100 |
| Anionic surfactant/lauric acid ratio | — | 2.1 | 2.1 |

A predispersion in selenium oil is prepared and is then mixed with the other ingredients.

The visual appearance of the formulations is noted. The formulation of Example 14 has a lighter colour than the oil-free formulations of Examples 12 and 13.

After preparing the compositions, their stability at 66° C. was studied by leaving them in an oven at this temperature for 1 week.

Figure 1:
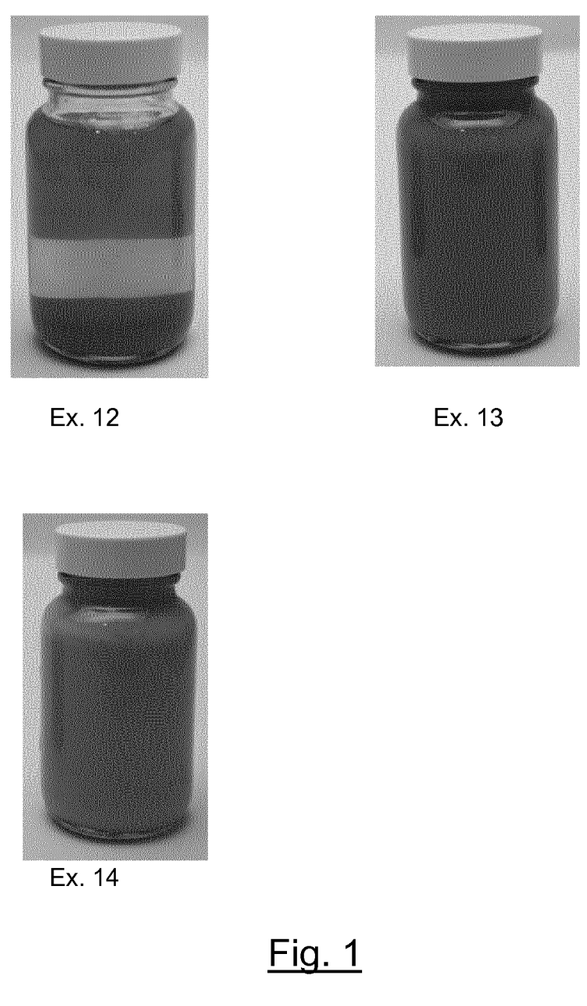

After one week, phase separation was observed, as indicated in FIG. 1, for the composition of Example 12 not comprising any lauric acid. The composition of Example 12 is therefore not stable under the test conditions. The compositions of Examples 13 and 14 according to the invention remain stable, without any trace of phase separation or decantation.

Example 15

The following compositions were prepared from those ingredients shown in Table 5 below. The amounts are expressed as % by weight of active substance based on the total weight of the composition.

TABLE 5

|  | A invention | B comparative |
|---|---|---|
| Cocamidopropyl betaine | 6.9 a.s. | 6.9 a.s. |
| Ammonium lauryl sulfate | 11.8 a.s. | 11.8 a.s. |
| Lauric acid | 5 | 3.4 |
| Salicylic acid | 0.2 | 0.2 |
| Sodium benzoate | 0.5 | 0.5 |
| Water | Balance to 100 | Balance to 100 |
| Sodium laureth sulfate | 1.15 a.s. | 1.15 a.s. |
| Polyquaternium-10 | 0.91 a.s. | 0.91 a.s. |
| Amodimethicone | 0.26 a.s. | 0.26 a.s. |
| Piroctone olamine | 0.5 | 0.5 |
| Anionic surfactants/Fatty acid Ratio | 2.6 | 3.8 |

Stability of the Compositions

In order to estimate their respective stability, each of the compositions A and B was put in an oven at 45° C. for 4 days.

Figure 2:
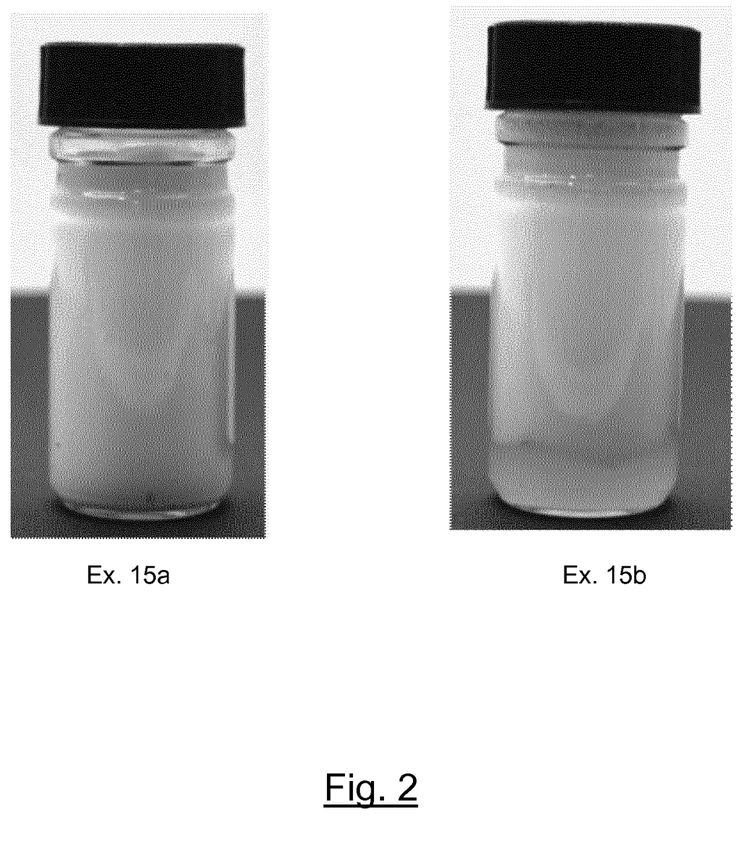

The results can be seen on FIG. 2.

It can be seen that the comparative composition B in which the ratio between anionic surfactants and fatty acids is higher than 3.5 is not stable, in contrast to the composition A according to the invention. During storing it was destabilized and separated into 2 distinct phases.

Thus, the compositions according to the invention having a weight ratio between anionic surfactants and fatty acid(s) from 0.5 to 3.5 result in having better stability with respect to compositions such as the comparative composition B.

The invention claimed is:

1. A cosmetic composition, comprising:
(i) at least one anionic surfactant chosen from ($C_6$-$C_{24}$) alkyl sulfates, ($C_6$-$C_{24}$)alkyl ether sulfates comprising from 1 to 50 ethylene oxide units, or a mixture of these compounds, wherein the anionic surfactant(s) is (are) present in an amount ranging from 11% to 15% by weight, relative to the total weight of the composition,
(ii) lauric acid present in an amount of 4% to 15% by weight, relative to the total weight of the composition, and
(iii) at least one antidandruff agent,
wherein the anionic surfactant/lauric acid weight ratio ranges from 0.5 to 3.5.

2. The cosmetic composition according to claim 1, wherein the at least one anionic surfactant is chosen from ($C_{12}$-$C_{20}$)alkyl sulfates, ($C_{12}$-$C_{20}$)alkyl ether sulfates comprising from 1 to 20 ethylene oxide units, or the salts of alkali metals, of ammonium, of amino alcohols, of alkaline-earth metals, or of sodium thereof; ammonium lauryl sulfate; or sodium lauryl ether sulfate.

3. The cosmetic composition according to claim 1, wherein an anionic surfactant/lauric acid weight ratio ranges from 1 to 3.

4. The cosmetic composition according to claim 1, wherein the at least one antidandruff agent is chosen from pyridinethione salts, 1-hydroxy-2-pyrrolidone derivatives, 2,2'-dithiobis(pyridine N-oxide), selenium sulfides, zinc pyridinethione, (1-hydroxy-4-methyl-6-(2,4,4-trimethylpentyl)-2-pyridone and salts thereof, selenium sulfides, or mixtures thereof.

5. The cosmetic composition according to claim 1, wherein the total amount of the at least one antidandruff agent ranges from 0.01% to 20% by weight, relative to the total weight of the composition.

6. The cosmetic composition according to claim 1, further comprising at least one amphoteric or zwitterionic surfactant chosen from ($C_8$-$C_{20}$)alkyl betaines and ($C_8$-$C_{20}$)alkylamido ($C_1$-$C_6$)alkyl betaines, in an amount ranging from 0.1% to 30% by weight, relative to the total weight of the composition.

7. The cosmetic composition according to claim 1, further comprising at least one nonionic surfactant chosen from ($C_6$-$C_{24}$ alkyl)-mono- or -polyglycosides, and oxyalkylenated fatty alcohols, in an amount ranging from 0.1% to 30% by weight, relative to the total weight of the composition.

8. The cosmetic composition according to claim 1, further comprising at least one non-silicone fatty substance other than lauric acid, chosen from oils of plant origin and liquid fatty esters.

9. The cosmetic composition according to claim 1, further comprising at least one cationic polymer in an amount ranging from 0.01% to 10% by weight, relative to the total weight of the composition.

10. The cosmetic composition according to claim 1, further comprising at least one silicone in an amount ranging from 0.01% to 10% by weight, relative to the total weight of the composition.

11. The cosmetic composition according to claim 1, wherein the at least one anionic surfactant is in the form of alkali metal, ammonium, amino alcohol and alkaline-earth metal salts.

12. A cosmetic process for treating keratin fibres, the process comprising:
applying to said fibres of an effective amount of a cosmetic composition comprising:
(i) at least one anionic surfactant chosen from ($C_6$-$C_{24}$) alkyl sulfates, ($C_6$-$C_{24}$)alkyl ether sulfates comprising from 1 to 50 ethylene oxide units, or a mixture of these compounds, wherein the anionic surfactant (s) is (are) present in an amount ranging from 11% to 15% by weight, relative to the total weight of the composition,
(ii) lauric acid present in an amount of 4% to 15% by weight, relative to the total weight of the composition, and
(iii) at least one antidandruff agent,
wherein the anionic surfactant/lauric acid weight ratio ranges from 0.5 to 3.5; and
rinsing and drying said fibres.

13. The process according to claim 12, wherein the at least one anionic surfactant is in the form of alkali metal, ammonium, amino alcohol and alkaline-earth metal salts.

* * * * *